(12) United States Patent
Nafie et al.

(10) Patent No.: US 7,522,283 B2
(45) Date of Patent: Apr. 21, 2009

(54) METHODS AND APPARATUS FOR THE IMPROVED MEASUREMENT OF CIRCULAR AND LINEAR DICHROISM AND USES THEREOF

(75) Inventors: Laurence A. Nafie, Cicero, NY (US); Henry Buijs, Quebec (CA)

(73) Assignee: Biotools, Inc., Jupiter, FL (US)

( * ) Notice: Subject to any disclaimer, the term of this patent is extended or adjusted under 35 U.S.C. 154(b) by 262 days.

(21) Appl. No.: 11/358,531

(22) Filed: Feb. 21, 2006

(65) Prior Publication Data

US 2006/0139650 A1    Jun. 29, 2006

(51) Int. Cl.
   *G01B 9/02*    (2006.01)
   *G01J 3/45*    (2006.01)
(52) U.S. Cl. .................................. 356/453; 250/339.08
(58) Field of Classification Search ................. 356/451, 356/453, 339.07; 250/339.08, 339.09
   See application file for complete search history.

(56) References Cited

U.S. PATENT DOCUMENTS

| | | | | |
|---|---|---|---|---|
| 3,728,030 | A | 4/1973 | Hawes | 356/106 |
| 4,095,900 | A * | 6/1978 | Murphy et al. | 356/456 |
| 5,450,196 | A | 9/1995 | Turner | 356/346 |
| 5,808,739 | A | 9/1998 | Turner et al. | 356/346 |
| 6,233,054 | B1 | 5/2001 | Theriault | 356/451 |
| 6,469,790 | B1 | 10/2002 | Manning | 356/451 |
| 6,480,277 | B1 | 11/2002 | Nafie | 356/364 |

OTHER PUBLICATIONS

Griffiths et al, Fourier Transform Infrared Spectrometry, 1986, pp. 286-297.*
"Fourier Transform Infrared Spectrometry" by Peter R. Griffiths and James A. deHaseth, *A Wiley-Interscience Publication*, pp. 143-147 (1986).
"Vibrational Optical Activity of Pharmaceuticals and Biomolecules" by Rina K. Dukor and Laurence A. Nafie, Encyclopedia of Analytical Chemistry: Applications, Theory and Instrumentation, pp. 661-676 (2000).
"Vibrational CD Spectrometers" by Laurence A. Nafie, *Encyclopedia of Spectroscopy and Spectrometry*, pp. 2391-2402 (1999).
"Vibrational Optical Activity Theory" by Laurence A. Nafie and Teresa B. Freedman, Circular Dichroism: Principles and Applications, Second Edition, pp. 97-131 (2000).

(Continued)

*Primary Examiner*—Patrick J Connolly
(74) *Attorney, Agent, or Firm*—David G. Rosenbaum; J. Peter Parades; Rosenbaum & Associates, PC (57) ABSTRACT

The present invention is directed generally to an apparatus and methods that combine a novel four-port dual-source interferometer with double modulation FT-VCD or FT-VLD measurements to obtain a spectrometer with enhanced signal quality (S/N), and lower susceptibility to detector saturation. In the novel apparatus of the present invention, a linear polarizer or tandem array of identically-oriented polarizers is placed in front of each of the two sources in a four-port dual-source interferometer, with the polarization state of one of the linear polarizers (or tandem array of polarizers) vertical and the polarization state of the other linear polarizer (or tandem array of polarizers) horizontal, i.e., with the polarization axes of the polarizers orthogonal to one another. Methods for measuring these spectra using the various aspects of the apparatus of the present invention are also provided.

18 Claims, 5 Drawing Sheets

OTHER PUBLICATIONS

"Infrared and Raman Vibrational Optical Activity: Theoretical and Experimental Aspects" by Laurence A. Nafie, *Ann. Rev. Phys. Chem.*, vol. 48, pp. 357-386 (1997).

"Theory of High Frequency Differential Interferometry: Application to the Measurement of Infrared Circular and Linear Dichroism via Fourier Transform Spectroscopy" by L. Nafie and M. Diem, *Applied Spectroscopy*, vol. 33, No. 2, pp. 130-135 (1979).

"Vibrational Circular Dichroism in the Mid-Infrared Using Fourier Transform Spectroscopy" by Lipp et al., *Chemical Physics Letters*, vol. 90, No. 1, pp. 1-5 (Jul. 1982).

"Fourier Transform Infrared Circular Dichroism: A double modulation approach" by L.A. Nafie, et al., *SPIE*, vol. 289, pp. 457-468 (1981).

"Biological and Pharmaceutical Applications of Vibrational Optical Activity" by Laurence A. Nafie and Teresa B. Freedman, pp. 15-54 (2000).

"Vibrational Circular Dichroism" by L. Nafie et al., *Handbook of Vibrational Spectroscopy*, pp. 731-744 (2002).

"Dual Polarization Modulation: A Real-Time, Spectral-Multiplex Separation of Circular Dichroism from Linear Birefringence Spectral Intensities" by Laurence A. Nafie, *Applied Spectroscopy* vol. 54, No. 11, pp. 1634-1645 (2000).

"Differential Absorption of High Modulation Frequencies Using a Fourier Transform Infrared Spectrometer" by L.A. Nafie and D.W. Vidrine, *SIPE*, vol. 191, pp. 56-63 (1979).

\* cited by examiner

Figure 1A

*Prior Art*

METHODS AND APPARATUS FOR THE IMPROVED MEASUREMENT OF CIRCULAR AND LINEAR DICHROISM AND USES THEREOF

CROSS-REFERENCE TO RELATED APPLICATIONS

This application claims priority to pending PCT International Application Serial No. PCT/US2004/027402 filed Aug. 23, 2004, which claims priority to provisional patent application Ser. No. 60/496,796, filed Aug. 21, 2003.

BACKGROUND OF THE INVENTION

Vibrational circular dichroism (VCD) and vibrational linear dichroism (VLD) are sensitive spectroscopic probes of molecular structure that reveal detailed information about the spatial and stereo-specific organization of matter at the molecular level. The great technological advances of our age, for the genomic and proteomic revolutions in biology, and the miniaturization of electronics and new materials of physics and chemistry, depend on our understanding of matter at the level of individual molecules. As our understanding of the world at this level grows deeper, our ability to control our environment, our communications, and our health increases dramatically.

Despite the usefulness of VCD and VLD, the measurement of these spectra is associated with poor signal-to-noise (S/N) ratios because of the small spectral intensities often associated with such difference in measurements. As a result, novel methods of improving S/N ratios in these measurements are of considerable interest as a result of making such measurements faster and/or of higher quality.

This is particularly true for Fourier transform (FT) infrared VCD (FT-VCD), i.e., the difference in absorbance of a molecule for left versus right circularly polarized radiation, where intensities are commonly in the range $10^{-4}$ to $10^{-6}$ absorbance units. See Nafie (1997), *Ann. Rev. Phys. Chem.*, 48:357; Nafie (1999) in *Encyclopedia of spectroscopy and Spectrometry*, J. C. Lindon, G. E. Trantor, J. L. Holmes, Eds. (Academic Press, Ltd., London), p. 2391; Dukor and Nafie (2000), in *Encylopedia of Analytical Chemistry: Instrumentation and Applications*, R. A. Meyers, Ed. (John Wiley and Sons, Chichester), p. 662; Nafie and Freedman (2000), in *Circular Dichroism: Principles and Applications, Second Edition*, K. Nakanishi, N. Berova, R. Woody, Eds. (Wiley-VCH, New York), p. 97; Nafie and Freedman (2000), in *Infrared and Raman Spectroscopy of Biological Materials*, H.-U. Gremlich, B. Yan, Eds. (Marcel Dekker, Inc., New York), p. 15; Nafie et al. (2002), in *Handbook of Vibrational Spectroscopy*, J. M. Chalmers, P. R. Griffiths, Eds. (John Wiley & Sons, Chichester,), p. 731; and, Nafie (2000), *Appl. Spectrosc.* 54:1634. S/N is also problematic for another form of spectroscopic measurement, Fourier transform vibrational linear dichroism (FT-VLD).

An obvious way to improve signal quality in such situations is to increase the instrumental throughput for a given spectral region of measurement. However, high throughput presents only a limited solution to S/N problems, in light of detector non-linearity at high infrared intensity levels.

There is therefore a need for methods and instruments for improving S/N ratios in FT-VCD and FT-VLD determinations. The present invention addresses this need for FT-VCD and FT-VLD determinations. The present invention additionally addresses the need for circular and linear dichroism determinations at wavelengths other than the infrared, e.g., at visible/ultra-violet wavelengths.

SUMMARY OF THE INVENTION

The present invention is directed to a novel four-port dual-source interferometer apparatus, and various embodiments thereof, for use in the determination of the Fourier Transform (FT) absorbance of a sample in a particular spectral region, i.e., in a particular wavelength range. The wavelength ranges contemplated in the present invention include, but are not limited to: the visible wavelengths of light; the ultraviolet ("UV") wavelengths of light; and, the infrared ("IR") wavelengths of light, including the near-infrared, the mid-infrared, and the far-infrared regions of the infrared. The present invention is also directed to methods for conducting such determinations using the interferometer apparatus of the present invention.

Thus one embodiment of the present invention is directed to a novel four-port dual-source interferometer comprising two light sources of matched spectral range. A second embodiment of the present invention is directed to the novel interferometer apparatus of the present invention further comprising cube-corner mirrors in the optical path. A third embodiment of the present invention is directed to the novel interferometer apparatus of the present invention further comprising both cube-corner mirrors and orthogonally-disposed polarizers in the optical path of the interferometer. A fourth embodiment of the present invention is directed to the novel interferometer apparatus of the present invention further comprising cube-corner mirrors, orthogonally-disposed polarizers in the optical path of the interferometer, and a photoelastic modulation (PEM) double modulation component. This embodiment is useful for circular and linear dichroism measurements in various spectral regions, and is contemplated to be particularly useful for FT-VCD and FT-VLD spectra.

The present invention is also directed to methods of using the various embodiments of the apparatus of the present invention in spectral determinations.

BRIEF DESCRIPTION OF THE DRAWINGS

The foregoing summary, as well as the following detailed description of preferred embodiments of the invention, will be better understood when read in conjunction with the appended drawings. For the purpose of illustrating the present invention, there are shown in the drawings embodiments which are presently preferred. It should be understood, however, that the invention is not limited to the precise arrangements and instrumentalities shown.

FIG. 1A shows a conventional single-source interferometer comprising a radiation source (S), two plane mirrors (M), and a beamsplitter (BS). FIG. 1B shows a novel dual-source interferometer comprising two radiation sources ($S_A$ and $S_B$), two cube-corner mirrors (CCM), and a suitable beamsplitter (BS). In this dual-source interferometer, reflections of the radiation beams occur at each cube-corner mirror such that the outgoing parallel beam is displaced relative to the incoming beam without changing the linear polarization state of the beam.

DETAILED DESCRIPTION OF THE INVENTION

The present invention is directed to a novel four-port dual-source interferometer apparatus, and various embodiments thereof, for use in the determination of the Fourier Transform (FT) absorbance of a sample in a particular spectral region, i.e., in a particular wavelength range. As discussed above, this novel four-port dual-source interferometer apparatus and methods using this apparatus offer enhanced signal quality (i.e., improved signal-to-noise, "S/N"), and lower susceptibility to detector saturation.

With general regard to standard interferometer design, most interferometers have two ports, an input port for radiation from the source and an output port for the beam going to the sample. See, e.g., FIG. 1A. See also Griffiths and Haseth (1986), *Book Fourier Transform Infrared Spectrometry*, (John Wiley & Sons, Inc., New York), and Chamberlin (1979), *Book Principles of interferometric Spectrosopy*, (John Wiley & Sons, Inc., New York).

However, an interferometer may also be designed as a four-port dual-source instrument. Such interferometers may be constructed if the plane mirrors of a conventional interferometer are replaced by cube-corner mirrors (CCM). See, e.g., FIG. 1B. In such an interferometer, the incident beam from the source is directed to the lower half of the beamsplitter (BS). There, in the usual fashion, the source beam is divided into a transmitted beam, $I_T$, and a reflected beam, $I_R$, and directed to the lower half of the two cube-corner mirrors of the interferometer. Each optical ray undergoes three reflections, one off each of the three surfaces of the cube-corner mirror, and returns along a path exactly parallel to its incident path to the upper half of the beamsplitter. Here the two beams recombine and interfere to create two output beams from the interferometer, $I_{TR+RT}$ and $I_{TT+RR}$. One of these beams, typically, $I_{TR+RT}$, travels to the sample region and the other, $I_{TT+RR}$, travels back toward the source.

Figure 1A:
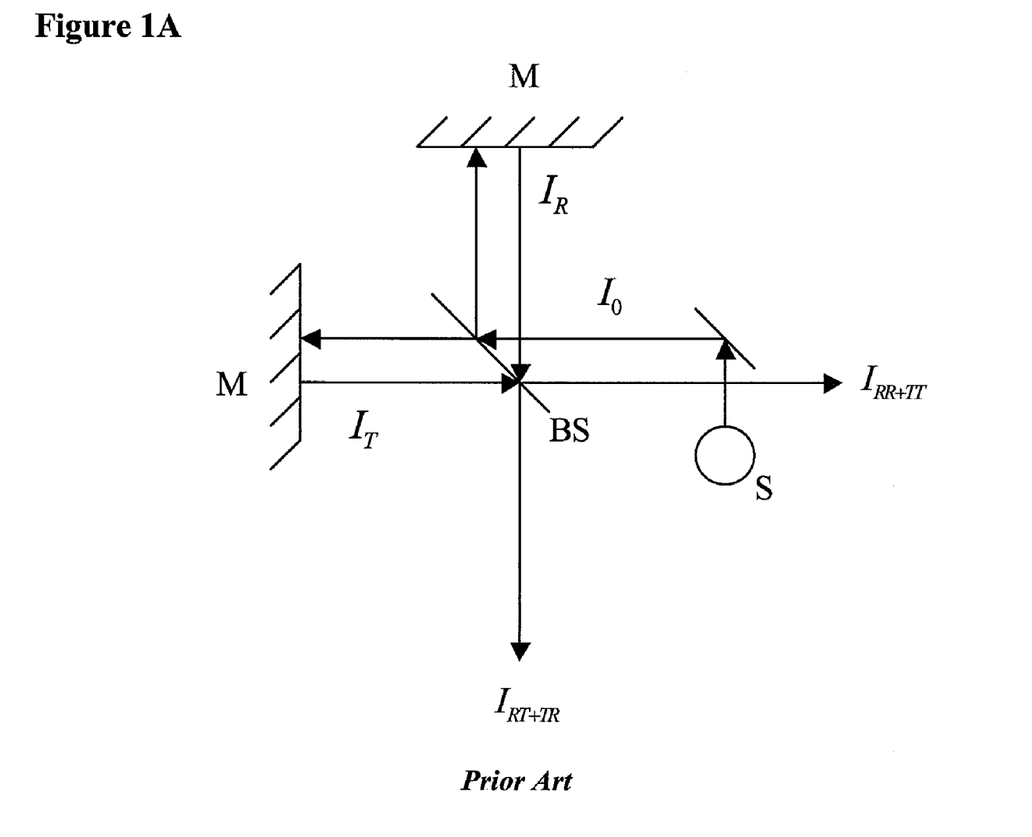
FIG. 1A-B illustrates the optical layout of a conventional single-source (FIG. 1A) or dual-source (FIG. 1B) interferometer. Specifically.
Figure 1B:
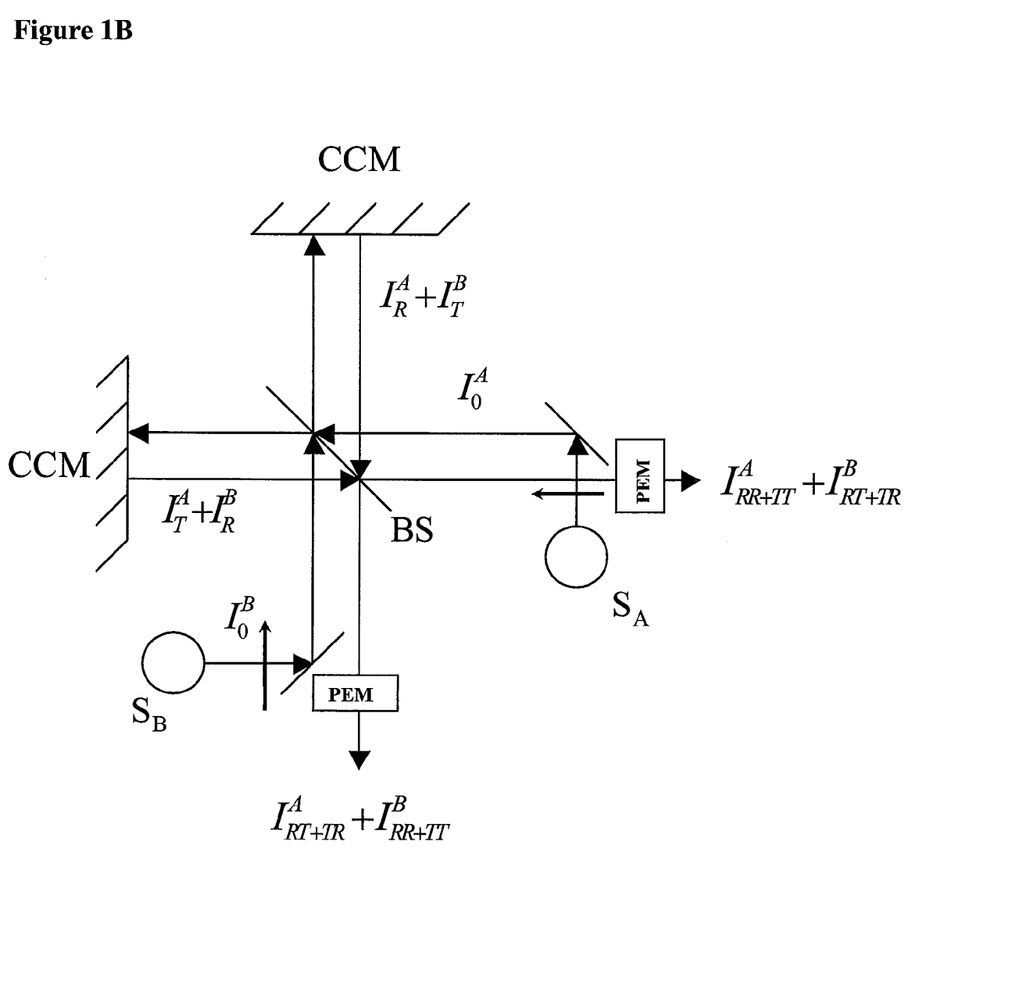

In a single-source, dual-port interferometer, only the sample beam is available; in contrast, in a dual-source, four-port (synyonymously, "four-port dual-source") cube-corner interferometer, where the source beam is confined to the lower half of the interferometer, both beams are available on the upper half of the optical layout. With this design, it is possible to construct an interferometer with two sources with inputs on the lower level of the interferometer and two output beams on the upper level. The interferometer is symmetric with respect to the directions of the input and output beams. Typically either one source or the other is used, but it is noted that the output beams of the two sources are out of Fourier phase with respect to one another along a given output beam path. If both sources are operated at the same time, their interferograms tend to cancel to the degree that the two sources have the same output modulation intensity and spectral profile. The beams used in a four-port dual-source interferometer are illustrated in FIG. 1B.

Thus one embodiment of the present invention is directed to a novel four-port dual-source interferometer. As used herein, the term "four-port dual-source interferometer" (synonymously, the "interferometer," "interferometer apparatus," or "apparatus" of the present invention) refers generally to the novel four-port dual-source interferometer of the present invention in which the two sources of the interferometer produce light of matched spectral range (i.e., range of light wavelengths produced), but not necessarily of identical intensity. By contrast, "conventional interferometer" or "conventional two-port single-source interferometer" refers to a conventional two-port single-source interferometer such as is shown in FIG. 1A and discussed in Examples 1 and 4 below.

In the novel four-port dual-source interferometer of the present invention, the two sources of the interferometer produce light of matched spectral range, (i.e., range of light wavelengths produced), but not necessarily of identical intensity. In this regard, for example, the present invention contemplates an interferometer apparatus in which the two sources are of identical material, such that the spectrum of radiation produced from the first source is matched to the spectrum of radiation from the second source of the interferometer. For example, when the apparatus of the present invention is to be used for measurements in the IR region of the spectrum (i.e., for FT-IR measurements such as FT-VCD or FT-VLD), the light sources of the present invention are those that the skilled artisan would understand to be appropriate emitters of light in the IR region of the spectrum, e.g., a light source fabricated of silicon carbide ("SiC"). For other spectral ranges of interest, the sources will be chosen such that their spectral emission properties are appropriate for measurements in those spectral ranges.

In this regard, the wavelength ranges contemplated for use with the novel four-port dual-source interferometer apparatus and methods of the present invention include, but are not limited to: the ultraviolet ("UV") or visible wavelengths of light, as would be used in the determination of FT electronic circular dichroism ("FT-ECD," or, synonymously, "CD") or FT electronic linear dichroism ("FT-ELD"); and, the infrared ("IR") wavelengths of light, including the near-infrared, the mid-infrared, and the far-infrared regions of the infrared, as would be used in the determination of FT vibrational circular dichroism ("FT-VCD") or FT linear dichroism ("FT-LCD"). The skilled artisan will understand that the use of any particular wavelength region for measurement may alter the requirements for the components of the four-port dual-source interferometer of the present invention. For example, it maybe necessary to use optical components that are optimized for the particular frequency region of spectral determination. Such optimization is well within the abilities of one of ordinary skill in the art. The present invention is also directed to methods for conducting such determinations using the interferometer apparatus of the present invention.

A second embodiment of the present invention is directed to the novel interferometer apparatus of the present invention further comprising cube-corner mirrors ("CCMs") in the optical path, e.g., the apparatus shown diagrammatically in FIG. 1B, and discussed in Example 2 below. The skilled artisan will understand that, by reference to the discussion of Example 2, the precise details of the choice of optical components and arrangement of these components in this embodiment will be determined by the necessity in this embodiment of generating the two output beams given in Eqs. 4 and 5 of Example 2. Thus the skilled artisan will understand that this embodiment is specially intended to encompass any four-port dual-source interferometer (as described previously) comprising cube-corner mirrors that is capable of generating the output beams given in Eqs. 4 and 5 of Example 2.

A third embodiment of the present invention is directed to the novel interferometer apparatus of the present invention further comprising both cube-corner mirrors and orthogonally-disposed polarizers in the optical path of the interferometer, e.g., the apparatus discussed in Example 3 below. In this embodiment, at least one linear polarizer is placed in front of each of the two light sources of the four-port dual-source interferometer (i.e., at any position between the light source and the beamsplitter of the interferometer apparatus), with the linear polarizer in front of one light source oriented such that its polarization axis is orthogonal to the polarization axis of the linear polarizer in front of the other light source.

The present invention contemplates that one linear polarizer may be used in each beam between the light source and the beamsplitter of the apparatus. Alternatively, the present invention contemplates that more than one linear polarizer may be interposed in each of the beams, as long as the linear polarizers in such a multiple array are arranged such that their polarization axes are approximately parallel, i.e., such that they are not off-axis to such a degree that there is insufficient light passing through the tandem array of linear polarizers. Thus the tandem array of linear polarizers contemplated herein does not include an array of linear polarizers where the polarization axes are crossed to produce essentially complete light attenuation. When multiple linear polarizers are used in tandem in each light path, it will also be necessary that the two arrays are orthogonal to one another, i.e., that the presence of multiple linear polarizers in each of the two light-source beams produces the same results as are obtained by the use of orthogonally-disposed single linear polarizers in the two beams.

As for the embodiment of Example 2, one of ordinary skill in the art will understand that, by reference to the discussion of Example 3, the precise details of the choice of optical components and arrangement of these components in this third embodiment of the apparatus of the invention will be determined by the necessity in this embodiment of generating the two output beams given in Eqs. 6 and 7 of Example 3. Thus the skilled artisan will understand that this embodiment is specially intended to encompass any four-port dual-source interferometer comprising cube-corner mirrors and orthogonally-disposed linear polarizers that is capable of generating the output beams given in Eqs. 6 and 7 of Example 3.

A fourth embodiment of the present invention is directed to the novel interferometer apparatus of the present invention further comprising cube-corner mirrors, orthogonally-disposed polarizers in the optical path of the interferometer, and a photoelastic modulation (PEM) double modulation component, with this embodiment useful for either circular or linear dichroism measurements, including: electronic circular and linear dichroism measurements (i.e., ECD and ELD measurements); and, vibrational (infrared) circular and linear dichroism measurements (i.e., VCD and VLD measurements), as given in, respectively, Examples 5 and 6.

In this regard, the use of double modulation PEM-based methods for circular and linear dichroism measurements was developed for conventional interferometers over twenty years ago. See Nafie (2000), *Appl. Spectrosc.*, 54:1634; Nafie and Vidrine, *Proc. Soc. Photo. Inst. Eng.*, 191:56 (1979); Nafie et al. (1981), in *Proceedings of the 1981 International Conference on Fourier Transform Infrared Spectroscopy*, J. Sakal, Ed. (SPIE, Vol. 289, 1981), p. 457; and, Lipp et al. (1982), *Chem. Phys. Lett.*, 90:1. As applied to, for example, vibrational circular dichroism (VCD), in the double-modulation method the infrared beam is first polarized linearly at 45 degrees to the stress axis of a photoelastic modulator (PEM) that converts the polarization state of the light to left and right circular states at the PEM frequency, typically in the tens of kHz frequency range. The beam then passes through a chiral sample and on to a semi-conductor detector that can follow the high-frequency polarization modulation signal. The signal at the detector has two kinds of intensity modulation, one at the Fourier frequencies associated with the unpolarized IR spectrum and one at the PEM modulation frequency associated with the VCD spectrum. To measure VCD, the signal is first demodulated at the PEM frequency and the resulting VCD interferogram is Fourier transformed to yield the VCD spectrum. If the linear polarizer prior to the PEM is rotated by 90 degrees, right (RCP) and left circular polarization (LCP) states of radiation are interchanged and the resulting VCD spectrum has the opposite sign for all of its bands. The double modulation method can also be applied to the measurement of vibrational linear dichroism (VLD) in an analogous way, using instead modulation of the IR beam between vertically and horizontally polarized radiation, and the rotation of the linear polarizer by 90 degrees changes the sign of the VLD spectrum as well. See Nafie and Diem (1979), *Appl. Spectrosc.*, 33:130; Dowrey and Marcott (1982), *Appl. Spectrosc.*, 36:414; and, Nafie (1988), in *Advances in Applied FTIR Spectroscopy*, M. W. Mackenzie, Ed. (John Wiley & Sons, New York), p. 67.

Thus as discussed above, the fourth embodiment of the present invention is directed to the novel interferometer apparatus of the present invention further comprising cube-corner mirrors, orthogonally-disposed polarizers in the optical path of the interferometer, and a photoelastic modulation (PEM) double modulation component, with this embodiment useful for either circular or linear dichroism measurements, including: electronic circular and linear dichroism measurements (i.e., ECD and ELD measurements); and, vibrational (infrared) circular and linear dichroism measurements (i.e., VCD and VLD measurements), as given in, respectively, Examples 5 and 6. This embodiment of the apparatus of the invention offers distinct advantages in terms of S/N and detector saturation, as discussed elsewhere herein.

The following Examples provide additional detail on the various embodiments of the apparatus of the present invention, as well as examples of the use of these embodiments of the apparatus of the present invention in the methods of the invention for measuring circular or linear dichroism, particularly at infrared wavelengths.

EXAMPLE 1

Analytical Framework for a Conventional Two-Port Single-Source Interferometer

The analysis in this Example is directed to a conventional two-port single-source interferometer, i.e., a conventional interferometer (such as a conventional infrared interferometer) equipped with a single source. An optical diagram of such an interferometer is given in FIG. 1A. This diagram shows the beams produced by the source (S) when passing through the optical paths provided by the mirrors (M) and beamsplitter (BS) of the interferometer, specifically one beam, $I_{RT+TR}$ (synonymously the "2RT" beam), going to the sample position, the other, $I_{RR+TT}$, returning to the source. In this nomenclature, the $I_{RT+TR}$ beam traveling to the sample has experienced either reflection (R) followed by transmission (T), or the reverse, at the beamsplitter; in contrast, the $I_{RR+TT}$ beam traveling back toward the source has experienced either two reflections or two transmissions at the beamsplitter. The intensities of these two beams may be expressed as given in Eqs. 1 and 2:

$$I_{RT+TR}(\delta) = 2a_T a_R I_0 - 2a_T a_R \int_0^\infty I_0(\bar{v}) e^{2\pi i \delta \bar{v}} d\bar{v} \quad (1)$$

$$I_{RR+TT}(\delta) = (a_R^2 + a_T^2) I_0 + 2a_T a_R \int_0^\infty I_0(\bar{v}) e^{2\pi i \delta \bar{v}} d\bar{v} \quad (2)$$

$$I_{RT+TR}^A(\delta) + I_{RR+TT}^B(\delta) = \frac{1}{2}(I_0^A + I_0^B) - \frac{1}{2} \int_0^\infty [I_0^A(\bar{v}) - I_0^B(\bar{v})] e^{2\pi i \delta \bar{v}} d\bar{v} \quad (4)$$

$$I_{RR+TT}^A(\delta) + I_{RT+TR}^B(\delta) = \frac{1}{2}(I_0^A + I_0^B) + \frac{1}{2} \int_0^\infty [I_0^A(\bar{v}) - I_0^B(\bar{v})] e^{2\pi i \delta \bar{v}} d\bar{v} \quad (5)$$

In these equations, $\delta$ is the interferometer beam-path difference, and $\alpha_R$ and $\alpha_T$ are, respectively, the reflective and transmissive beamsplitter efficiencies. In general, $\alpha_R$ and $\alpha_T$ have different values.

As shown in Eqs. 1 and 2, both the $I_{RT+TR}$ and $I_{RR+TT}$ beams have both a constant DC intensity component (i.e., the first term of Eqs. 1 and 2) as well as a Fourier-modulated AC intensity component (i.e., the second term of Eqs. 1 and 2), with the Fourier terms of the two beams out-of-phase with respect to each other and therefore given opposite signs. For simplicity, the present analysis assumes a constant value of the efficiency coefficients over the spectral range of interest, as well as a sum of $\alpha_R$ and $\alpha_T$ equal to unity. Given this latter constraint, it is clear that the sum of the two output beams equals the original source intensity, $I_0$. The effects of internal reflections within the beamsplitter are included in the transmission and reflection efficiency coefficients.

At the equal mirror position, i.e., where the interferometer beam-path difference $\delta$ is zero, the Fourier integrals in Eqs. 1 and 2 reduce to the integral of the intensity of the source:

$$I_0 = \int_0^\infty I_0(\bar{v}) d\bar{v} \quad (3)$$

Thus, as observed experimentally, at the equal mirror position all intensity returns to the source in the $I_{RR+TT}$ beam, and none appears at the sample in the $I_{RT+TR}$ beam. For unequal values of the transmission and reflection coefficients, the DC-component of the $I_{RR+TT}$ beam is always greater than that of the $I_{RT+TR}$ beam. On the other hand, the Fourier-modulated components of each of these intensities that arise from interference between the beams from returning from the two arms of the interferometer must be equal, and the amount of the radiation in the $I_{RT+TR}$ beam limits this Fourier-modulated intensity. The highest Fourier modulation efficiency occurs when $\alpha_R$ and $\alpha_T$ are equal to one another, with a value of ½.

EXAMPLE 2

Analytical Framework for the Novel Four-Port Dual-Source Interferometer of the Present Invention FIG. 1B shows an exemplary optical layout of the novel four-port dual-source interferometer of the present invention. Specifically, FIG. 1B shows an interferometer equipped with input sources A and B ($S_A$ and $S_B$), two cube-corner mirrors (CCM), and a beamsplitter (BS). In such an interferometer there are four output beams to consider, two from source A, and two from source B. Assuming equal reflection and transmission efficiency coefficients, the output beams passing by source B and by source A (see FIG. 1 B) are given by Eqs. 4 and 5, respectively:

As for Eqs. 1 and 2, in Eqs. 4 and 5 the two output beams are out of Fourier phase with respect to one another, and the sum of these two equations is the sum of the two total source intensities. In addition, the contributions of sources A and B in each of these two beams are also out of Fourier phase with respect to one another. If the two sources have the same total intensity and the same spectral profiles, namely $I_0^A(\bar{v}) = I_0^B(\bar{v})$, the Fourier integrals in Eqs. 4 and 5 vanish.

EXAMPLE 3

Analytical Framework for the Novel Four-Port Dual-Source Interferometer of the Present Invention Further Comprising Orthogonal Polarizers As discussed above, one embodiment of the present invention is directed to a four-port cube-corner-mirror interferometer where a linear polarizer is placed in front of each of the two sources A and B of the interferometer, and where these linear polarizers are positioned with their polarization axes orthogonal to one another. This Example provides the analytical framework for understanding this embodiment of the present invention.

Thus this Example is directed to the four-port dual-source interferometer of the present invention configured to contain orthogonally arranged (i.e., arranged such that their polarization axes are orthogonal to one another) linear polarizers after each radiation source, e.g., arranged such that the radiation from source A is vertically polarized with respect to the plane of the arms of the interferometer, while radiation from source B is horizontally polarized. The skilled artisan will understand that the present invention contemplates any method for producing two orthogonally polarized light sources, including the disposition of a single polarizer after source A and a single polarizer after source B, as well as the disposition of more than one polarizer in tandem after source A and more than one polarizer in tandem after source B. In light of this discussion, it is therefore understood that "a" polarizer as contemplated herein is intended to encompass both one unitary polarizer, and multiple polarizers in tandem, as discussed.

Given the orthogonal arrangement of polarizers discussed above, for, e.g., source A, the efficiency coefficients for reflection and transmission at the beamsplitter are those for s-polarized radiation with respect to the surface of the beamsplitter, while for source B the efficiency coefficients are those for p-polarized radiation. In general, the efficiency coefficients for s- and p-polarized radiation for reflection and transmission are not equal to one another, resulting in four efficiency coefficients that must be included in an analytic framework. An analysis of the behavior of the polarizer-containing apparatus of the present invention involving the generalization of Eqs. 4 and 5 to include these four efficiency coefficients is shown in Eqs. 6 and 7:

$$I_{RT+TR}^A(\delta) + I_{RR+TT}^B(\delta) = 2a_R^s a_T^s I_0^A + [(a_R^p)^2 + (a_T^p)^2]I_0^B - \qquad (6)$$
$$\int_0^\infty [2a_R^s a_T^s I_0^A(\bar{v}) - 2a_R^p a_T^p I_0^B(\bar{v})]e^{2\pi i\delta\bar{v}} d\bar{v}$$

$$I_{RR+TT}^A(\delta) + I_{RT+TR}^B(\delta) = 2a_R^p a_T^p I_0^B + [(a_R^s)^2 + (a_T^s)^2]I_0^A + \qquad (7)$$
$$\int_0^\infty [2a_R^s a_T^s I_0^A(\bar{v}) - 2a_R^p a_T^p I_0^B(\bar{v})]e^{2\pi i\delta\bar{v}} d\bar{v}$$

Here again the sums of the transmission and reflection coefficients for s- and p-polarized radiation are both unity:

$$\alpha_R^s + \alpha_T^s = \alpha_R^p + \alpha_T^p = 1 \qquad (8)$$

For these expressions, the sum of the two equations is simply the integrated sum of the two sources. The interferograms are equal and opposite and the contributions of each source to the interferograms of each beam are opposite. If all four efficiency coefficients in Eq. 8 are equal to ½, Eqs. 6 and 7 reduce to Eqs. 4 and 5. In general, for Eqs. 6 and 7 there are two ways in which the ordinary infrared-intensity interferograms can avoid vanishing: if the source intensities and profiles are different; and, if the corresponding efficiency coefficients of the beamsplitter for s- and p-polarized radiation are not the same. In general, the products $\alpha_R^s \alpha_T^s$ and $\alpha_R^p \alpha_T^p$ are not equal. Therefore, even if the two sources are matched to be equal, the transmission interferograms in Eqs. 6 and 7 will not vanish.

EXAMPLE 4

Analytical Framework for Conventional Two-Port Single-Source Vibrational Circular Dichroism (VCD) Determination One aspect of the present invention is directed to methods for improving signal to noise in the measurement of vibrational circular dichroism (VCD), and to apparatus useful in such methods. This Example provides an analytical framework for understanding the apparatus and methods of the present invention for VCD determination by developing an analytical framework for the use of conventional single-source VCD measurement apparatus using a photoelastic modulator (PEM) to implement the double modulation method of VCD determination.

Thus as discussed previously, measurement of Fourier transform VCD (FT-VCD) is conventionally performed using the double modulation method, with a PEM placed in the beam after a linear polarizer and before the sample. If the sample is chiral, there will be differences in the transmitted light at the PEM modulation frequency due to differences in the absorbance of the sample for left versus right circularly polarized radiation. Thus at the detector there will be DC terms and Fourier-modulated terms, as discussed above, as well as terms that are double-modulated at the Fourier frequencies and the PEM frequency. The interferogram associated with the VCD is obtained by demodulating the double-modulated term with respect to the PEM frequency using a lock-in amplifier tuned to this frequency. The output of the lock-in with a sufficiently fast time-constant (typically in the microsecond range) yields the VCD interferogram.

If VCD detection and a chiral sample is added to the setup described by Eq. 1, the total intensity expression after demodulation of the polarization-modulation interferogram at the PEM frequency is:

$$I_{TR+RT}(\delta) = 2a_T a_R I_0 - 2a_T a_R \int_0^\infty I(\bar{v})e^{2\pi i\delta\bar{v}} d\bar{v} - \qquad (9)$$
$$2a_T a_R \int_0^\infty I(\bar{v})2J_1[\alpha(\bar{v})]1.1513\Delta A(\bar{v})e^{2\pi i\delta\bar{v}} d\bar{v}$$

The absorbance $A(\bar{v})$ of the sample is defined by the expression:

$$A(\bar{v}) = -\log_{10}[I(\bar{v})/I_0(\bar{v})] \qquad (10)$$

and VCD is defined as:

$$\Delta A(\bar{v}) = A_L(\bar{v}) - A_R(\bar{v}) \qquad (11)$$

In Eq. 9, $J_1[\alpha(\bar{v})]$ is the PEM efficiency with respect to VCD measurement as a function of wave number frequency. The wave number frequency of the maximum of $J_1[\alpha(\bar{v})]$ can be set by adjusting the level of the PEM voltage. The first two terms in Eq. 9 are the same as those in Eq. 1 for the IR interferogram. The third term in Eq. 9 is the VCD interferogram. The VCD spectrum can be isolated in a three-step process by separately Fourier transforming the second and third terms in Eq. 9, dividing the Fourier transform (FT) of the third term by the FT of the second term, and, finally, by removing the Bessel function dependence by dividing by an appropriate calibration curve, $2J_1[\alpha(\bar{v})]1.1513$, the procedure for the measurement of which has been published previously. See Nafie et al. (1981), in *Proceedings of the 1981 International Conference on Fourier Transform Infrared Spectroscopy*, J. Sakal, Ed. (SPIE, Vol. 289), p. 457, and Nafie (1988), in *Advances in Applied FTIR Spectroscopy*, M. W. Mackenzie, Ed. (John Wiley & Sons, New York), p. 67. This procedure is expressed as:

$$\Delta A(\bar{v}) = \frac{FT\left[2a_T a_R \int_0^\infty I(\bar{v})2J_1[\alpha(\bar{v})]1.1513\Delta A(\bar{v})e^{2\pi i\delta\bar{v}} d\bar{v}\right]}{FT[2a_T a_R \int_0^\infty I(\bar{v})e^{2\pi i\delta\bar{v}} d\bar{v}]2J_1[\alpha(\bar{v})]1.1513} \qquad (12)$$

EXAMPLE 5

Analytical Framework for Vibrational Circular Dichroism (VCD) Determination Using the Novel Four-Port Dual-Source Interferometer with Orthagonal Polarizers of the Present Invention As discussed previously, one aspect of the present invention is directed to methods for improving signal to noise in measurement of vibrational circular dichroism (VCD), and to apparatus useful in such methods. This Example provides an analytical framework for understanding VCD determination using the inventive four-port dual-source interferometer with orthogonal polarizers described in, e.g., Example 3 above.

Thus with regard to VCD determination using the dual-polarizer apparatus of the present invention, the VCD interferogram obtained from this apparatus may be described by generalizing the situation for the single-source case of VCD measurement presented in Eq. 9 of Example 4 above using the analytical framework for dual polarizers presented in Eqs. 6 and 7 of Example 3, with the following results:

$$[I_{RT+TR}^A(\delta) + I_{RR+TT}^B(\delta)]_{VCD} = \qquad (13)$$
$$-\int_0^\infty [2a_R^s a_T^p I^A(\bar{v}) + 2a_R^p a_T^p I^B(\bar{v})] 2J_1[\alpha(\bar{v})]\Delta A(\bar{v})e^{2\pi i\delta\bar{v}} d\bar{v}$$

$$[I_{RR+TT}^A(\delta) + I_{RT+TR}^B(\delta)]_{VCD} = \qquad (14)$$
$$\int_0^\infty [2a_R^s a_T^p I^A(\bar{v}) + 2a_R^p a_T^p I^B(\bar{v})] 2J_1[\alpha(\bar{v})]\Delta A(\bar{v})e^{2\pi i\delta\bar{v}} d\bar{v}$$

As shown in Eqs. 13 and 14, the two terms that depend on the beamsplitter efficiency coefficients and the infrared intensities due to the two sources now combine by addition, rather than by subtraction as found in the non-VCD dual-source example shown in Eqs. 6 and 7. This difference in behavior for VCD measurements occurs because the VCD contributions from the two sources have opposite signs due to the orthogonal orientations of their polarizers; in contrast, for ordinary infrared intensity or absorbance spectrum determination, the relative orientation of the polarizers has no such effect. As demonstrated above, the two sources carry intrinsically opposite Fourier phase for their contributions to a given output beam; therefore, the VCD contributions from each source add rather than subtract. It is interesting to note that the VCD interferograms associated with the two output beams, namely those in Eqs. 13 and 14, are identical in magnitude but opposite in sign.

Finally, the expected magnitude of the VCD intensity from dual-source operation, $[\Delta A(\bar{v})]_{DS}$, may be compared to that of single source operation $[\Delta A(\bar{v})]_{SS}$, where the latter is given by Eq. 12. Since the VCD intensity involves dividing the VCD transmission spectrum by the corresponding infrared transmission spectrum, as illustrated in Eq. 12, the following relationship holds:

$$[\Delta A(\bar{v})]_{DS} = \frac{a_R^p a_T^p I^A(\bar{v}) + a_R^s a_T^s I^B(\bar{v})}{|a_R^p a_T^p I^A(\bar{v}) - a_R^s a_T^s I^B(\bar{v})|} [\Delta A(\bar{v})]_{SS} \qquad (15)$$

This ratio is the sum of two positive terms divided by the positive difference of these same two terms. It is independent of wavenumber frequency, assuming wavenumber-independent efficient coefficients, and is the same for each of the two output beams from the four-port, dual-source interferometer. Because the efficiency coefficients are defined as positive numbers, the ratio is always greater than unity for unequal contributions from sources A and B. The ratio reduces to unity if either source is turned off, the sign of the denominator, before taking the absolute value, being immaterial physically as it is always positive following Fourier transformation with appropriate phase correction. There is no limit to the increase in the magnitude of the measured dual-source uncalibrated VCD intensity relative to single-source uncalibrated VCD intensity as the denominator in Eq. 15 approaches zero.

Another numerical measure of dual-source to single-source operation efficiency is the comparison of the magnitude of the dual-source infrared transmission intensity to either of the two single-source infrared transmission intensities, such as for comparison to source A:

$$\frac{I_{TR+RT}^A(\bar{v}) + I_{RR+TT}^B(\bar{v})}{I_{TR+RT}^A(\bar{v})} = \frac{|a_R^s a_T^s I^A(\bar{v}) - a_R^p a_T^p I^B(\bar{v})|}{a_R^s a_T^s I^A(\bar{v})} \qquad (16)$$

and analogously for comparison to source B. Measurement of the magnitudes of the two single-source intensity interferograms allows prediction of the magnitude of the dual-source interferogram.

EXAMPLE 6

Analytical Framework for Vibrational Linear Dichroism (VLD) Determination Using the Novel Four-Port Dual-Source Interferometer with Orthogonal Polarizers of the Present Invention Example 5 provides above provides an analysis of the measurement of VCD using the apparatus of the present invention. An analysis similar to that of Example 5 may be performed for vibrational linear dichroism (VLD).

Specifically, in the case of VLD, a linearly dichroic sample is used. Such a sample has a difference in absorption intensity for orthogonally polarized linear polarization states. Therefore the sample requires some degree of macroscopic orientation, and must possesses one or more internal axes of alignment. Examples are a stretched polymer film or fiber, or grazing-angle incidence and reflection off a surface with adsorbed molecules, the latter case often being referred to as infrared reflection absorption spectroscopy (IRRAS). Dowrey and Marcott (1982), *Appl. Spectrosc.*, 36:414. Dual-source operation is analogous for VCD and VLD because changing the orientation of polarizer by 90° prior to the PEM changes the sign of the entire VLD spectrum. The only changes in these expressions are the usual ones when comparing expressions for VCD and VLD, namely the VLD spectrum depends on $J_2[\alpha(\bar{v})]$ instead of $J_1[\alpha(\bar{v})]$ and the VLD interferogram is present at the harmonic of (twice) the PEM frequency instead of the fundamental of the PEM frequency. With these changes, Eqs. 13 and 14 can be rewritten for VLD as:

$$[I_{RT+TR}^A(\delta) + I_{RR+TT}^B(\delta)]_{VLD} = \qquad (17)$$
$$-\int_0^\infty [2a_R^s a_T^p I^A(\bar{v}) + 2a_R^p a_T^p I^B(\bar{v})] 2J_2[\alpha(\bar{v})]\Delta A(\bar{v})e^{2\pi i\delta\bar{v}} d\bar{v}$$

$$[I_{RR+TT}^A(\delta) + I_{RT+TR}^B(\delta)]_{VLD} = \qquad (18)$$
$$\int_0^\infty [2a_R^s a_T^p I^A(\bar{v}) + 2a_R^p a_T^p I^B(\bar{v})] 2J_2[\alpha(\bar{v})]\Delta A(\bar{v})e^{2\pi i\delta\bar{v}} d\bar{v}$$

and the S/N ratio increases described in Eqs. 15 and 16 for VCD apply equally well to VLD when the absorbance difference intensity $\Delta A(\bar{v})$ represents VLD instead of VCD.

EXAMPLE 7

Experimental Measurements—Data

FT-VCD measurements were carried out on the ChiralIR from BioTools, Wauconda, Ill. and ABB-Bomem, Quebec, Canada, equipped for dual source operation with a four-port cube-corner mirror interferometer and a ZnSe photoelastic modulator (PEM) operating at 37 kHz. Infrared radiation was detected with a liquid-nitrogen-cooled MCT detector having a low-frequency cut-off approximately 800 cm$^{-1}$. The beamsplitter was constructed from uncoated ZnSe. The interferometer was equipped with two sources, A and B. Source A was in the normal source position and had a BaF$_2$ wire grid polarizer placed in front of it to pass vertically polarized radiation with respect to the plane of the interferometer. For reflection or transmission with respect to the plane of the beamsplitter, the radiation from this source is s-polarized. Source B is located beneath the beam port that normally goes to the sample. The radiation is horizontally polarized and corresponds to p-polarized radiation at the beamsplitter. VCD and IR spectra of S-(−)-α-pinene were measured at 4 cm$^{-1}$ resolution employing standard VCD spectral collection and calibration software on the ChiralIR spectrometer. Samples of S-(−)-α-pinene were purchased from the Aldrich Chemical Company and used without further purification.

Figure 2:
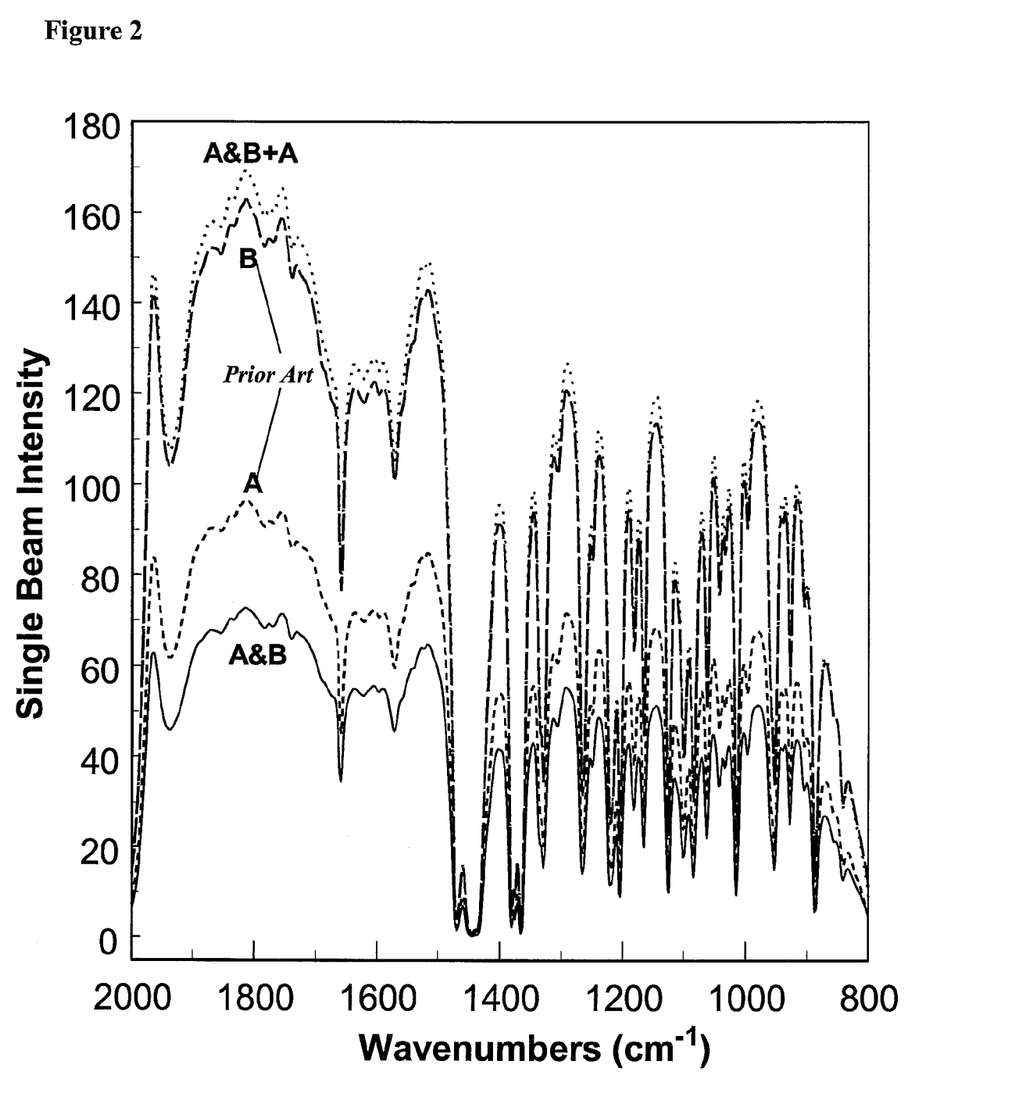
FIG. 2 provides single-source (A and B) and dual-source (A&B) single-beam infrared transmission spectra of S-(−)-pinene, neat in 69 μm, 4 cm$^{-1}$ resolution. The calculated curve labeled A&B+A can be compared to single-source curve B.

The results of single-beam IR transmission measurements in arbitrary units for a sample of S-(−)-α-pinene are shown in FIG. 2. Specifically, this figure shows the relative intensities obtained for source A (labeled "A" in FIG. 2), source B (labeled "B" in FIG. 2) and both sources A and B, (labeled "A&B" in FIG. 2). It is clear that reduced single-beam transmission is obtained in the case of two sources corresponding to the difference in the single-beam transmission spectra for source A and source B. In addition, FIG. 2 provides a combined curve labeled A&B+A that can be compared directly to curve B since source A contributes negatively to the A&B intensity since (B−A)+A equals B. Under normal operating conditions, the single-beam transmission for source A for the spectral region between 2000 and 800 cm$^{-1}$ saturates the detector. With a sample of α-pinene in place, source B does not saturate the detector; however, the transmission level is not far from saturation. The small difference in the transmission for curves A&B+A and B arises from the onset of saturation in the case of single-beam transmission with source B alone. This difference is not due to any thermal decay of either source A or B as the source configuration of the instrument is changed.

The values of the peak intensity of the single-beam infrared transmission curves near 1800 cm$^{-1}$ are given in Table I for the four curves in FIG. 2. The intensity reduction factors, predicted from Eq. 16 for dual-source operation relative to source A and source B, respectively, are given by $$\frac{|a_R^s a_T^s I^A(\bar{v}) - a_R^p a_T^p I^B(\bar{v})|}{a_R^p a_T^p I^B(\bar{v})} = \frac{|98-162|}{162} = 0.40 \qquad (17)$$

$$\frac{|a_R^s a_T^s I^A(\bar{v}) - a_R^p a_T^p I^B(\bar{v})|}{a_R^s a_T^s I^A(\bar{v})} = \frac{|98-162|}{98} = 0.65 \qquad (18)$$

Comparison to the measured reduction figures of $72/162=0.44$ and $72/98=0.73$ confirm dual source operation as formulated theoretically.

Figure 3:
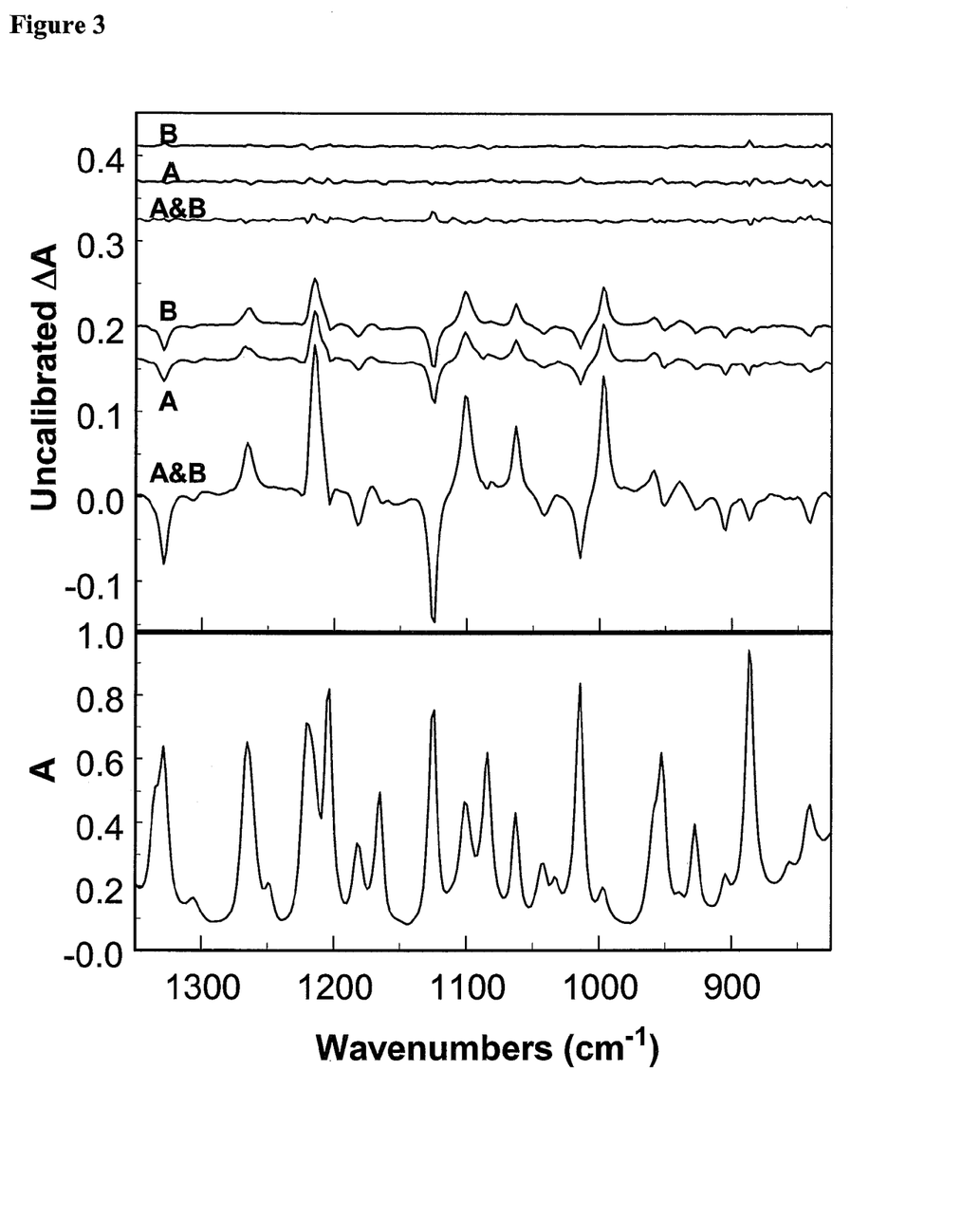
FIG. 3 provides uncalibrated VCD and noise spectra (upper panel) and absorbance spectra (lower panel) for sources A, B, and A&B for a sample of neat S-(−)-pinene in a 69 μm cell at 4 cm$^{-1}$ resolution and a collection time of 20 minutes for each source configuration.

Comparison of the uncalibrated VCD spectra (ratio of VCD transmission to IR transmission without calibration) from single-source (SS) and dual-source (DS) operation is given in FIG. 3 for the S-(−)-α-pinene sample in FIG. 2. From the intensity values in Table I, and using Eq. 15, an increase in the VCD intensity for DS-operation relative to SS-operation (for either source A or B) is predicted to be as follows:

$$[\Delta A(\bar{v})]_{DS} = \frac{a_R^s a_T^s I^A(\bar{v}) + a_R^p a_T^p I^B(\bar{v})}{|a_R^s a_T^s I^A(\bar{v}) - a_R^p a_T^p I^B(\bar{v})|} [\Delta A(\bar{v})]_{SS} \qquad (19)$$

$$= \frac{98+162}{|98-162|}[\Delta A(\bar{v})]_{SS}$$

$$= (4.0)[\Delta A(\bar{v})]_{SS}$$

The level of increase is verified in FIG. 3 and in Table I where the increase in size for the DS-VCD spectrum is 3.6 relative to that of each of the SS-VCD measurements.

Also displayed in FIG. 3 are the noise curves for each of these measurements. The noise at the detector is constant for each of these measurements under the expected assumption of background-noise limited operation of the MCT detector. The VCD noise curve is not the same for each of these three measurements since the un-normalized VCD transmission, at constant noise, is divided by the single-beam IR transmission of the instrument with the sample in place in order to remove instrument-scale dependence from the VCD measurement, as in Eq. 12. This normalization favors higher infrared transmission intensity (smaller apparent noise due to division by a larger transmission intensity) over lower intensity, and thus the noise for operation with single-source A is greater than that for source B (the source with higher transmission), and the noise for DS operation is the largest of the three since it has the smallest transmission. However, the gain in VCD intensity for DS-operation significantly outweighs the smaller increase in the VCD noise (vide infra).

Figure 4:
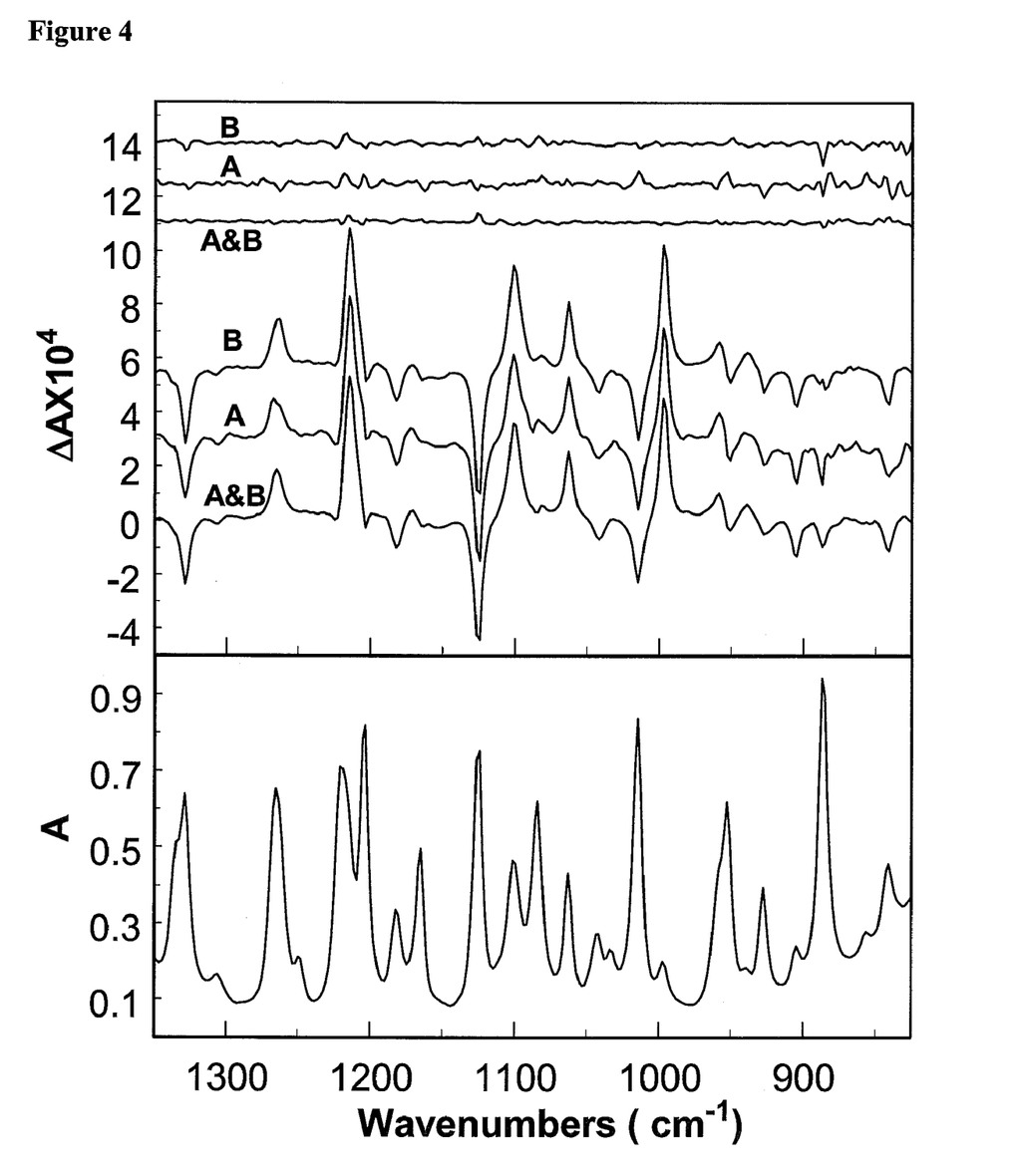
FIG. 4 provides calibrated VCD and noise spectra (upper panel) and absorbance (lower panel) for sources A, B and A&B of S-(−)-pinene, neat in 69 μm cell, at 4 cm$^{-1}$, and collection time for each source configuration of 20 minutes.

FIG. 4 presents the absorbance and final calibrated VCD spectra with noise curves for the S-(−)-α-pinene for all three source settings. In this figure, all three VCD measurements, properly calibrated, yield the same VCD intensity. The only difference now is the noise level. A clear advantage is seen for DS operation, with source B the next best and source A, the weaker source, the worst result. The DS improvement in signal-to-noise ratio scales as the sum of the two source intensities over the single source intensity of reference. Relative to source A and source B, these advantages are:

$$\frac{a_R^s a_T^s I^A(\bar{v}) + a_R^p a_T^p I^B(\bar{v})}{a_R^s a_T^s I_0^A(\bar{v})} = \frac{98+162}{162} = 1.6 \qquad (20)$$

$$\frac{a_R^s a_T^s I^A(\bar{v}) + a_R^p a_T^p I^B(\bar{v})}{a_R^s a_T^s I_0^B(\bar{v})} = \frac{98+162}{98} = 2.7 \qquad (21)$$

The decrease in collection time for DS operation over SS operation to achieve the same signal-to-noise ratio scales is the square of these advantages, namely 2.6 relative to source A and 7.3 relative to source B.

EXAMPLE 8

Experimental Measurements—Analysis

The four-port dual-source interferometer used for the measurements presented in Example 7 above is the standard optical layout for the MB-line (for example MB-100) of medium resolution FT-IR spectrometers from ABB Bomem. There are two source positions, cube-corner mirrors, and fast collection optics. The efficiencies in signal-to-noise ratio for normal single-source operation are at the state-of-the-art level and are in no way compromised by modification of this apparatus to the novel four-port dual-source optical layout of the present invention.

More specifically, the optical modification needed for the novel four-port dual-source VCD operation described in the present invention comprises the placement of polarizers with orthogonal relative orientations after the sources in order to appropriately polarize the light emanating from the sources. In addition to using the simultaneous dual-source operation for VCD, two sources in one instrument has been used for normal FT-IR absorption measurements with two different sources; for example, one for the mid-IR and one for the near-IR have been used. The sources were not used at the same time, and one can choose which source and spectral region to study.

It could be argued that the efficiency of the interferometer is decreased by the use of only the lower part of the beamsplitter for the beams coming into the beamsplitter and the use of only the uppermost part of the beamsplitter for beams emanating from the beamsplitter. In this regard, however, if the source is intercepted and collimated by a mirror that is sufficiently small and close to the source, the same solid angle of light coming from the source can be captured and directed to the beamsplitter as that by a larger mirror placed further away and designed to fill the entire beamsplitter with collimated light from the source. This is the basic principle of optical miniaturization whereby a smaller spectrometer can be designed to perform without loss of efficiency provided that all dimensions are scaled accordingly.

It is clear from FIGS. 2 through 4 that the theoretical description of a four-port dual-source interferometer given above is verified with experimental measurements. In particular, it was determined that, for ordinary infrared intensity measurements, the two sources in the common output beam, corresponding to Eq. 6, interfere with each other to reduce the magnitude of the observed interferogram. In addition, Eqs. 6 and 13 are verified for DS-VCD measurement where the magnitude of the observed uncalibrated VCD is increased relative to that for SS-VCD measurement by the ratio of additive contributions of the two sources to the subtractive contributions of the two sources, as given by Eq. 15.

The increase in the signal-to-noise ratio of the DS-VCD relative to the SS-VCD in FIG. 3 is due the additivity of the VCD intensities coming from the two sources without an increase in the noise contribution from the detector. From the experimental results in FIGS. 2 to 4, it can be concluded that the contribution of source B is greater than that for source A by the ratio of approximately 1.0 to 0.6. When, for VCD, the sources combine, the VCD signal increases without any increase in the accompanying noise. The signal-to-noise ratio therefore increases in this case by a factor of 1.6 compared to that of source B (not the normal source position for the output beam used) and a factor of 2.7 relative to source A (the normal source position for this output beam). This is equivalent to a decrease in spectral collection time, to achieve the same signal-to-noise ratio, of 2.6 relative to the corresponding SS-VCD measurement with source B and a reduction of 7.3 relative to the SS-VCD measurement with source A. These are very significant reductions in collection times that demonstrate a significant advantage to DS-VCD measurement compared to that of SS-VCD measurement.

A second intrinsic advantage of DS-operation is the reduction of the large interferogram associated with the ordinary IR spectrum. The reduction of the magnitude of the interferogram intensity allows the normal saturation level of the detector to be avoided. In particular, for the spectra presented in FIGS. 2 and 3, the intensity level of the stronger source, source B, without a sample in place, is beyond the saturation limit of its single-source operation. Since a background intensity measurement is necessary to measure the absorbance of a sample, normally steps would need to be taken to reduce the level of this intensity. Thus, not only can source B be used at a level of spectral contribution that is beyond its saturation limit, the contribution of source A, the normal source position, is added to this. This gives access to an operating regime that is well beyond that of an equivalent SS-VCD spectrometer. In principle, one can envision increasing the strengths of the sources to arbitrarily large levels, such that both sources are well beyond the saturation limit, as long as the contributions of both sources are sufficiently well balanced to prevent their difference contribution from exceeding the normal SS saturation limit. There is however, an issue that remains unexplored to date that may effectively limit the intensity levels that can be accessed by each source. This is the possible saturation of the detectors by the constant, non-Fourier-modulated intensities given by the first two terms in Eqs. 6 and 7. For the experiments performed here and to date with dual-source VCD operation, no effects of detection saturation due to the non-Fourier modulated intensity at the detector have been found.

An interesting limit of the advantage of four-port dual-source operation is when the contributions of the two sources are the same level. In this case, the DS-IR interferogram cancels and the DS-VCD doubles compared to either SS-VCD interferogram. The doubling of the VCD interferogram signal against a constant noise background leads to a doubling of the SNR and an improvement in signal averaging time of 4. Another way of stating this advantage is that the VCD spectrometer operating in DS mode under these conditions is equivalent to four such instruments operating in parallel for the same time of collection. Equal contributions from each source also maximizes the suppression of interferogram saturation since, in fact there is no normal IR intensity spectrum. At the same time, this limit is rather inconvenient since the single-beam IR interferogram is needed to obtain the proper VCD spectrum, in accordance with Eq. 12. Hence, for exactly matched sources, some other method, such as an aperture or screen in one of the source beams, is necessary to unbalance the source intensities and obtain the single-beam IR spectrum.

Finally, a number of observations may be made regarding the ease of alignment and the quality of the VCD baseline for dual-source versus single-source operation. In general, adjusting the baseline is simpler with one source compared to two. For the alignments to date where this has been carried out, the quality of the baseline achieved for two sources is the same as that obtainable with a single source. A particular concern might be the effect of moving the linear polarizer from just before the PEM in the standard single-source layout to a polarizer directly in front of each of the two sources for dual-source operation. For dual-source operation good linear polarization must be maintained over a number of mirror reflections prior to reaching the PEM. The directions of the two source polarizations are chosen to correspond to either pure s- or pure p-reflections at each mirror surface, (i.e., vertical or horizontal), and there does not appear to be any significant loss of these pure linear polarization states between the polarizers and the PEM. While the overall alignment is more difficult, there is an additional degree of freedom that can be utilized before arriving at the final alignment, namely the baseline of the second source can be used to balance that of the first source. Finally, the quality of any baseline achieved with dual-source operation can be improved by roughly one order of magnitude by using a dual-PEM setup as described in detail in an earlier publication from this laboratory. Nafie (2000), *Appl. Spectrosc.*, 54:1634. The three VCD spectrometers in our laboratory at Syracuse University spanning the mid-IR to the near-IR from 800 to 10,000 cm$^{-1}$ are all configured with two sources and two PEMs for optimum signal-to-noise ratio and baseline quality.

EXAMPLE 9

Experimental Measurements—Conclusions

The present invention is directed to the development of a novel spectroscopic method, dual-source Fourier transform polarization difference spectroscopy, and to various apparatus for implementing this method. The method, which is equally applicable to circular dichroism and linear dichroism measurement, is achieved by introducing orthogonally oriented polarizers in front of two sources in a four-port interferometer. The two source locations (used one at a time) and four-port cube-corner-mirror interferometer is the standard configuration of the MB series of FT-IR and FT-NIR spectrometers available from ABB Bomem. The novel design and use of a polarized dual-source, four-port interferometer of the present invention for VCD operation are described theoretically and experimentally. The advantages of the interferometer and method of the present invention include an additive contribution of VCD (or VLD) intensities from the two sources with respect to a fixed detector noise limit (for background limited noise operation), and a subtractive contribution of the IR intensities from the two sources, thus avoiding saturation limits normally encountered in single-source operation.

TABLE I

Single-Beam Transmission and Uncalibrated VCD Intensities

| Source | Single-Beam Transmission | Uncalibrated VCD* |
|---|---|---|
| A | 98 | 0.09 |
| B | 162 | 0.09 |
| A&B | 72 | 0.32 |
| A&B + A | 170 | — |

*VCD intensity measured as the intensity difference between the positive peak near 1220 cm$^{-1}$ and the negative peak near 1130 cm$^{-1}$.

While the present invention has been described with reference to its preferred embodiments, one of ordinary skill in the relevant art will understand that the present invention is not intended to be limited by these preferred embodiments, and is instead contemplated to include all embodiments consistent with the spirit and scope of the present invention as defined by the appended claims.

What is claimed is:

1. A dual-source interferometer comprising:
   a. a first light source including a first optical energy with a first optical spectrum range;
   b. a second light source including a second optical energy with a second optical spectrum range, wherein the second optical spectrum matches the first optical spectrum;
   c. a beamsplitter disposed to receive the first and second optical energies, wherein the beamsplitter splits the first optical energy into a first transmitted beam and a first reflected beam, and the beamsplitter splits the second optical energy into a second transmitted beam and a second reflected beam;
   d. a first mirror disposed to receive the first transmitted beam and the second reflected beam, wherein the first mirror reflects the first transmitted beam and the second reflected beam to the beamsplitter;
   e. a second mirror disposed to receive the first reflected beam and the second transmitted beam, wherein the second mirror reflects the first reflected beam and the second transmitted beam to the beamsplitter;
   f. the beamsplitter combining the first transmitted beam and the first reflected beam to produce a first output beam and a second output beam, and the beamsplitter combining the second transmitted beam and the second reflected beam to produce a third output beam and a fourth output beam;
   g. the first output beam and the second output beam traveling to a sample; and
   h. an optical detector to measure vibrational circular dichroism or vibrational linear dichroism of the sample.

2. The interferometer of claim 1 wherein the first mirror and the second mirror are cube-corner mirrors.

3. The interferometer of claim 2 wherein the first transmitted beam and second reflected beam undergo three reflections in the first cube-corner mirror to return along a path parallel to the incident path of the beamsplitter; and the first reflected beam and the second transmitted beam undergo three reflections in the second cube-corner mirror to return along a path parallel to the incident path of the beamsplitter.

4. The interferometer of claim 1 wherein the first optical energy includes a first intensity and the second optical energy includes a second intensity; and the first intensity is different than the second intensity.

5. The interferometer of claim 1 wherein the first optical spectrum range and the second optical spectrum range includes a wavelength of light from about the ultraviolet spectrum of light to the infrared spectrum of light.

6. The interferometer of claim 1 wherein the first optical energy and the second optical energy are out of Fourier phase.

7. The interferometer of claim 1 wherein the first and second output beams is given by the equation:

$$I^A_{RT+TR}(\delta) + I^B_{RR+TT}(\delta) = \frac{1}{2}(I^A_0 + I^B_0) - \frac{1}{2}\int_0^\infty [I^A_0(\bar{v}) - I^B_0(\bar{v})]e^{2\pi i \delta \bar{v}} d\bar{v}.$$

8. The interferometer of claim 1 wherein the third and fourth output beams is given by the equation:

$$I^A_{RR+TT}(\delta) + I^B_{RT+TR}(\delta) = \frac{1}{2}(I^A_0 + I^B_0) + \frac{1}{2}\int_0^\infty [I^A_0(\bar{v}) - I^B_0(\bar{v})]e^{2\pi i \delta \bar{v}} d\bar{v}.$$

9. The interferometer of claim 1 further comprising at least one linear polarizer disposed after the first light source, wherein the linear polarizer orients the first optical energy orthogonal to the second optical energy.

10. The interferometer of claim 9 further comprising at least one photoelastic modulator optically coupled to the interferometer to implement a double modulation.

11. A method for a four-port dual source interferometer, comprising the steps of:
   a. optically coupling a first light source including a first optical energy with a first optical spectrum range to a beamsplitter;
   b. optically coupling a second light source including a second optical energy with a second optical spectrum range to the beamsplitter, wherein the second optical spectrum matches the first optical spectrum;
   c. splitting the first optical energy into a first transmitted beam and a first reflected beam, wherein the first transmitted beam is split to a first mirror and the first reflected beam is split to a second mirror;

d. splitting the second optical energy into a second transmitted beam and a second reflected beam; wherein the second transmitted beam is split to the second mirror and the second reflected beam is split to the first mirror;

e. recombining the first transmitted beam with the second reflected beam to create a first output beam and a second output beam;

f. recombining the first reflected beam with the second transmitted beam to create a third output beam and a fourth output beam;

g. coupling the first output beam and second output beam to a sample; and h. measuring vibrational circular dichroism or vibrational linear dichroism of the sample with an optical detector.

12. The method of claim 11 wherein the first mirror comprises a first cube-corner mirror, wherein first transmitted beam and second reflected beam undergo three reflections in the first cube-corner mirror to return along a path parallel to the incident path of the beamsplitter; and the second mirror comprises a second cube-corner mirror, wherein the first reflected beam and the second transmitted beam undergo three reflections in the second cube-corner mirror to return along a path parallel to the incident path of the beamsplitter.

13. The method of claim 11 wherein the first optical spectrum range and the second optical spectrum range includes a wavelength of light from about the ultraviolet spectrum of light to the infrared spectrum of light.

14. The method of claim 11 wherein the first optical energy and the second optical energy are out of Fourier phase.

15. The method of claim 11 wherein the optically coupling steps further comprise optically coupling at least one linear polarizer disposed after the first light source, wherein the linear polarizer orients the first optical energy orthogonal to the second optical energy.

16. The method of claim 15 wherein the recombining steps further comprise optically coupling at least one photoelastic modulator.

17. The method of claim 11 wherein the first and second output beam is given by the equation:

$$I^A_{RT+TR}(\delta) + I^B_{RR+TT}(\delta) = \frac{1}{2}(I^A_0 + I^B_0) - \frac{1}{2}\int_0^\infty [I^A_0(\bar{v}) - I^B_0(\bar{v})]e^{2\pi i \delta \bar{v}} d\bar{v}.$$

18. The method of claim 11 wherein the third and fourth output beam is given by the equation:

$$I^A_{RR+TT}(\delta) + I^B_{RT+TR}(\delta) = \frac{1}{2}(I^A_0 + I^B_0) + \frac{1}{2}\int_0^\infty [I^A_0(\bar{v}) - I^B_0(\bar{v})]e^{2\pi i \delta \bar{v}} d\bar{v}.$$

* * * * *